United States Patent [19]

Burns et al.

[11] Patent Number: 4,476,707
[45] Date of Patent: Oct. 16, 1984

[54] GAS FLOW MEASUREMENT WITH DETENTED CHOPPER VALVE

[75] Inventors: Henry L. Burns, St. Helena; Erik W. Peterson, Calistoga, both of Calif.

[73] Assignee: Bear Medical Systems, Inc., Riverside, Calif.

[21] Appl. No.: 366,770

[22] Filed: Apr. 8, 1982

[51] Int. Cl.³ .......................... G01F 1/36; G01F 25/00
[52] U.S. Cl. ..................................... 73/4 R; 73/861.52
[58] Field of Search ........... 73/861.42, 861.47, 861.52, 73/708, 756, 4 R; 128/716, 720, 725

[56] References Cited

U.S. PATENT DOCUMENTS

| | | | |
|---|---|---|---|
| 3,296,868 | 1/1967 | Koppel et al. | 73/407 |
| 3,509,767 | 5/1970 | Greer | 73/398 |
| 3,740,533 | 6/1973 | Zeggelaar | 73/4 X |
| 3,765,239 | 10/1973 | Olsson | 73/194 R |
| 3,797,479 | 3/1974 | Graham | 128/2.08 |
| 3,924,612 | 12/1975 | Dempster et al. | 128/2.08 |
| 3,970,942 | 7/1976 | Mayer | 328/133 |
| 4,051,712 | 10/1977 | Zias et al. | 73/4 |
| 4,070,604 | 1/1978 | Usry | 318/203 A |
| 4,125,011 | 11/1978 | Porter | 73/4 |
| 4,271,701 | 6/1981 | Dempster et al. | 73/861.42 |
| 4,277,832 | 7/1981 | Wong | 364/510 |

FOREIGN PATENT DOCUMENTS

850750 10/1960 United Kingdom .

Primary Examiner—Herbert Goldstein
Attorney, Agent, or Firm—Howard J. Klein

[57] ABSTRACT

A gas flow measuring system employs an oscillating chopper valve alternately to deliver a flow head-generated pressure and a reference pressure to a pressure transducer. The chopper valve is driven by a stepping motor under the control of a microcomputer. The stepping motor drives the valve, with an oscillatory frequency determined by the microcomputer, between a first detented position, in which the flow head-generated pressure is delivered to the transducer, and a second detented position, in which the reference pressure is delivered to the transducer. The electrical signal produced by the transducer is fed to a sample-and-hold circuit, also under the control of the microcomputer, whereby the microcomputer controls the sampling rate of the sample-and-hold circuit. The microcomputer can thus establish an optimal sampling rate in accordance with the oscillatory frequency of the valve. In this manner, very fast sampling rates can be established, thereby minimizing the effects of zero drift in the transducer.

19 Claims, 6 Drawing Figures

FIG. 1

GAS FLOW MEASUREMENT WITH DETENTED CHOPPER VALVE

BACKGROUND OF THE INVENTION

This invention relates generally to gas flow measuring systems, and more particularly it relates to such systems of the open-end flow type, in which the flow in a conduit, known as a flow head, passes a restriction or obstruction in order to develop a pressure signal in proportion to flow through the conduit. Such systems have particular application in devices, known as spirometers, used for measuring pulmonary function.

In gas flow measuring systems of the type described generally above, and particularly in spirometers, the pressure differential developed in the flow head is communicated to a differential-pressure transducer which, in turn, produces an electrical signal which can be processed to yield values of flow rate and total flow volume through the flow head. In many applications, and particularly in spirometers, high degrees of accuracy are desired. It then becomes necessary to minimize errors which may be introduced into the system by the effects of ambient temperature changes and/or hysteresis on the mechanical components of the differential pressure transducer. Specifically, the typical pressure transducer provides for the pre-establishment of a point of reference from which to quantify the pressure measurement. However, this reference point can be caused to drift by such phenomena as hysteresis and ambient temperature changes, with resulting error in the pressure measurement. If, however, the reference point is sampled and re-established at intervals well within the time frame of the reference-point drift, suitable accuracy can be maintained.

The prior art has taken a number of approaches toward solving this problem of "zero drift." One approach has been the use of a mechanism which periodically "grounds" a pressure transducer to a predetermined reference pressure, while simultaneously driving the transducer output signal to a selected reference level. Examples of devices of this type are disclosed in U.S. Pat. No. 3,509,767—Greer; U.S. Pat. No. 3,765,239—Olsson: U.S. Pat. No. 3,924,612—Dempster et al.; and United Kingdom Pat. No. 850,750.

Another approach has been the use of a differential pressure transducer along with valving means for periodically reversing the pressure inputs to the transducer so as to produce an A.C. signal at the transducer's output. Electronic means are then used to determine the peak-to-peak value of the A.C. signal, the effects of zero drift thereby being nullified. Examples of this approach are found in U.S. Pat. No. 3,296,868—Koppel et al.; and U.S. Pat. No. 4,271,701—Dempster et al.

A common aspect of both of the approaches outlined above is the use of some valving mechanism which periodically and at regular intervals either "grounds" the transducer or reverses the "polarity" of the pressure inputs. In both cases, some means is required for detecting the state of this valving mechanism so that the reference point of the transducer output signal may be sampled and re-established in proper synchronism. Typically, such valve state detection mechanisms utilize optical, magnetic, and/or mechanical means for sensing the valve state, and some means for generating a valve state indicative signal for input to the synchronization circuit.

It will be appreciated that the need for such valve state detection mechanisms adds to the complexity of the overall apparatus, thereby increasing the costs thereof. Moreover, the accuracy and reliability of the valve state detection mechanism affects the overall accuracy and reliability of the gas flow measuring system in which it is incorporated. In addition, in such prior art devices, two separate mechanisms are used for, respectively, actuating the valving mechanism and detecting the valve state. This introduces another synchronization problem, with possible adverse effects on the reliability and accuracy of the overall system.

It will thus be appreciated that the need has been established for a gas flow measuring system capable of enhanced accuarcy and reliability through the simplification of the valve state detection mechanism and through the enhancement of the inherent accuracy of this mechanism. It will also be appreciated that it would be desirable to provide such enhanced reliability and accuracy with a mechanism which is relatively inexpensive to manufacture and which is simple to maintain in proper working condition.

SUMMARY OF THE INVENTION

Broadly described, the present invention is a gas flow measuring system in which a flow head is connected to a differential pressure transducer through an oscillating valve driven by a stepping motor under the control of a microcomputer. The first side or pressure inlet of the transducer receives a reference pressure while the second side or pressure inlet alternately receives the reference pressure or a signal pressure from the flow head, depending upon the state of the valve. Specifically, the valve has a first detented position in which it communicates the reference pressure to the second side of the transducer, and a second detented position in which it transmits flow head or signal pressure to the second side of the transducer. The valve member is caused to oscillate between these two detented positions by means of the stepping motor; thus, the valve state is a direct function of the rotational position of the stepping motor drive shaft, which itself oscillates between two positions under the control of the microcomputer. The microcomputer, in turn, is programmed to drive the stepping motor with a frequency determined by a real time clock oscillator. Since the microcomputer in effect drives the stepping motor, it can easily track the position of the stepping motor drive shaft and therefore the position of the oscillating valve element. In this manner, the present state of the oscillating valve is always "known" by the microcomputer, thereby eliminating the need for any separate valve state sensing mechanism.

The output signal from the pressure transducer is filtered and amplified and then fed to a sample-and-hold circuit, also under the control of the microcomputer, which can thereby establish the optimal sampling rate in accordance with the oscillatory frequency with which the oscillating valve is changing state between its reference pressure mode and its flow head pressure mode. The pressure signals received by the sample-and-hold circuit are then digitized and inputted to the microcomputer, where they are converted into signals indicative of flow rate and total instantaneous volume.

By the means briefly summarized above, both the sampling rate and the valve oscillation frequency can be selected so as to provide signal sampling at intervals well within the time frame of the expected zero drift.

Moreover, as will be made clear by the description which follows, the present invention allows for very fast sampling rates, so that pressure transducers which exhibit even quite significant degrees of zero drift can be used, thereby contributing to the overall economy of the system.

As will also be apparent from the detailed description which follows, contributing substantially to the overall performance of the system is the novel design of the oscillating valve. Briefly described, the oscillating valve (which will be referred to as a "chopper" valve), comprises a cylindrical valve body having a pair of generally radial input ports extending into a central cavity. Within the cavity is a rotary valving element having a radial bore which can be aligned with either of the two input bores, and an axial bore, communicating with the radial bore, and which is connected to the measuring side of the pressure transducer. The rotary element is connected to the drive shaft of the stepping motor, which, as previously mentioned, is under the control of a microcomputer. The stepping motor is magnetically detented into a predefined number of equiangular positions, although in this application only two adjacent positions are used. Under computer control, the stepping motor is oscillated between these two positions at a selected frequency, thereby oscillating the rotary valving element in a manner which brings its radial input bore alternately into communication with the two input bores of the body. In the present application, one of the valve body input bores is in communication with a reference pressure, while the other receives a signal pressure from the flow head. Thus, the measuring side of the pressure transducer alternately receives the reference pressure and the flow head pressure, with transitions between the two occurring at a frequency determined by the oscillating frequency of the stepping motor.

The oscillating motion of the valve between two discrete positions determined by the detented positions of the stepping motor allows the valve element movement to be continuously monitored by the microcomputer under the control of which the stepping motor is actuated. It is thus this feature which allows the system to dispense with the typical valve state detection mechanisms. Moreover, as will be made clear in the description below, the structure of the valve is such that the valve element is adapted for high-speed oscillation between its two detented positions, even with a relatively low-torque motor, thereby allowing high sampling rates. In addition, the valve is simply and economically constructed and is compact in size, thereby contributing to the overall economy of the system.

As will be better appreciated from the detailed description below, the present invention meets several heretofor unsatisfied needs of the prior art in providing a gas flow measuring system which is capable of achieving highly accurate measurements while using a simplified structure which enhances overall system reliability, and which is also amenable to economies in manufacturing costs.

DETAILED DESCRIPTION OF THE INVENTION

A preferred embodiment of the present invention is described herein and in the accompanying drawings. It should be kept in mind that the described embodiment is particularly suitable in a spirometer, and much of the description will assume use of the invention in such an application. However, those skilled in the pertinent arts will recognize that the described embodiment, with minor modifications, may be adapted to a wide variety of gas flow and pressure measurement applications.

Figure 1:
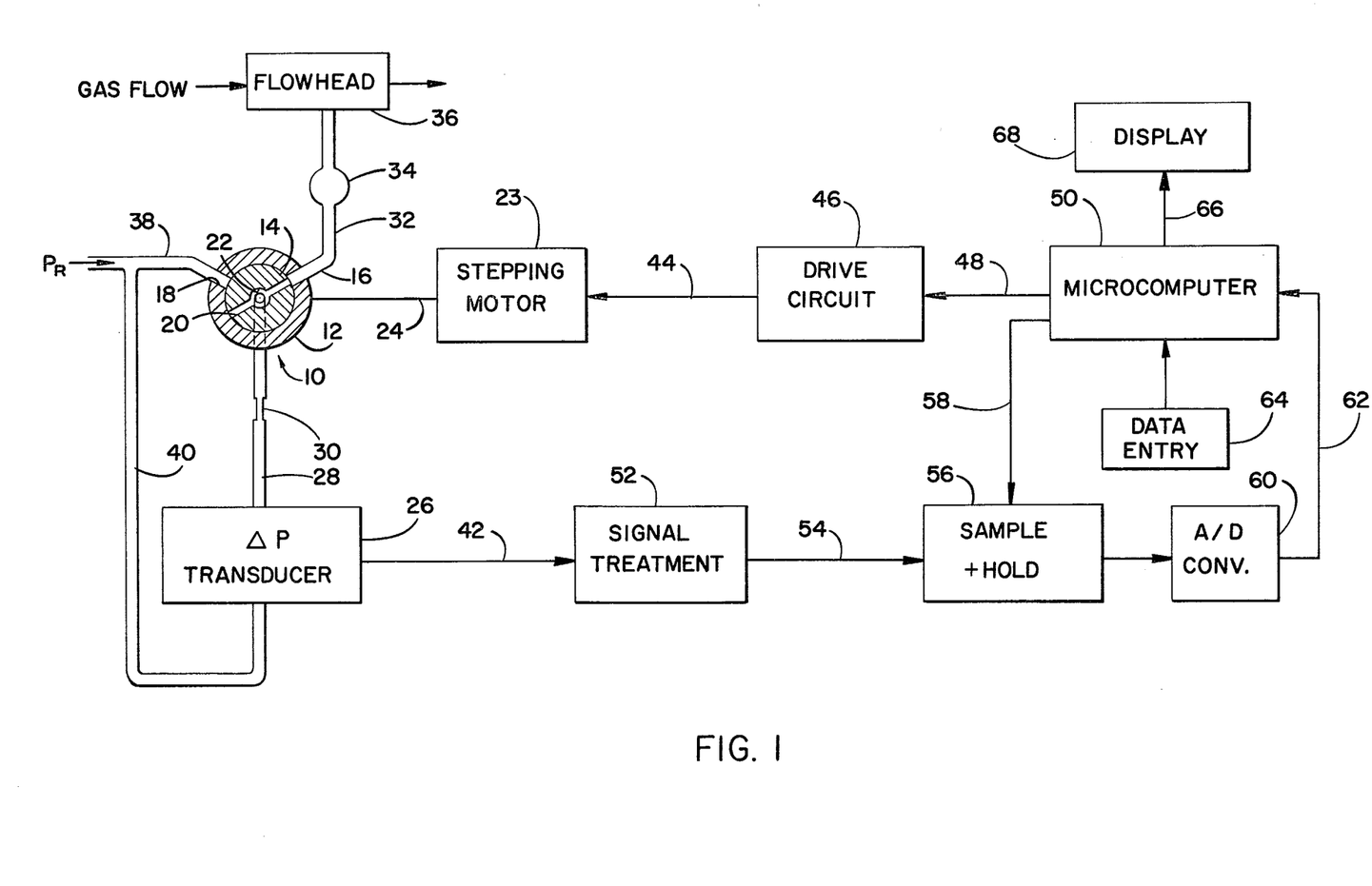
FIG. 1 is a schematic representation of a gas flow measuring system in accordance with the present invention.

FIG. 1 illustrates, in block diagram form, the basic components of a gas flow measuring system in accordance with the present invention. Each of the labeled blocks represents an electrical circuit or a mechanical assembly of a type which is well-known in the art, and will therefore be readily understood by those skilled in the pertinent arts without a tedious description of each component.

Central to the invention is an oscillating chopper valve 10, which will be described in detail hereinbelow. For the purposes of the present discussion, it is sufficient to describe the valve 10 as follows: An oscillating valving element 14 is encased within a generally cylindrical valve housing or body 12, having first and second radially directed inlets or pressure sensing ports 16 and 18, respectively. The valving element 14 has a radial passage or bore 20 extending diametrically therethrough and intersecting an axial passage or bore 22. The valving element 14 is adapted for axial rotation between two positions, in the first of which one end of the radial bore 20 is in communication with the pressure sensing port 16, and in the other of which the opposite end of the radial bore 20 is in communication with the pressure sensing port 18. The valving element 14 is oscillated between these two positions by a stepping motor 23 connected to the valving element 14 by means of a shaft, represented schematically by the line 24. Regardless of the position of the valving element 14, the axial bore 22 remains in constant fluid communication with one side (which may be referred to as the "signal side") of a differential pressure transducer 26, through a conduit 28 having a restriction 30 therein, the purpose of which will be described later on.

Coupled to the inlet port 16 by a conduit 32 having an enlarged diameter cavity 34 therein is a flow head 36, of the type which converts a fluid flow therethrough into a pressure which is communicated to the conduit 32. It will be understood that the flow head may be either of a an unidirectional or a bidirectional type, depending upon the particular application. The other pressure sensing port 18 is coupled by a conduit 38 to a source of reference pressure $P_r$, which in the case of a spirometer, may be ambient atmospheric pressure. The reference pressure is also communicated, through a conduit 40, to the side of the pressure transducer 26 opposite the signal side. This opposite side of the pressure transducer may be denominated the "reference side."

The differential pressure transducer 26 may be of any suitable type well-known in the art, but is preferably of the type having a piezoelectric element mounted on a flexible metal diaphragm. Flexing of the diaphragm (not shown) due to a pressure differential across it causes the piezoelectric element (not shown) to create an analog electrical signal which is transmitted from the transducer along an output line 42. In operation, when the valving element 14 is in the position in which the radial bore 20 is in communication with the reference pressure port 18, both sides of the differential pressure transducer 26 receive the reference pressure so that the pressure on both sides of the transducer is equalized. The pressure transducer 26 is thus, in effect, "grounded" to the reference pressure. This produces a reference level, or zero point, signal. When the valving element 14 is rotated so that the radial bore 20 is in communication with the signal pressure port 16, the signal side of the transducer 26 receives the pressure communicated from the flow head 36 through the conduit 32, the radial bore 20, the axial bore 22, and the conduit 28. With the reference side of the transducer 26 still receiving the reference pressure through the conduit 40, a differential pressure is set up within the transducer 26 which is translated into a pressure-indicative signal level or value in output line 42. The restriction 30 acts as a low pass filter which removes high frequency pressure transients from the conduit 28, thereby stabilizing the output signal of the pressure transducer 26. The enlarged diameter chamber or cavity 34 in the flow head pressure conduit 32 serves to damp reflected acoustic waves which may be propagated as a result of the action of the valving element 14. Such acoustic waves could, of course, distort the pressure signal received from the flow head 36.

As previously mentioned, the valving element 14 is oscillated between its two positions by the stepping motor 23 acting through the shaft 24. The stepping motor 23 is of the type, well-known in the art, whose armature is magnetically detented in a plurality of equiangular positions along its path of revolution. The stepping motor 23 must also be of the type which is reversible. An example of this type of motor is that made by Fuji Electrochemical Company of Japan under model number SM20-2004. In the example given, the detented positions are spaced apart by eighteen degrees (18°) of arc, and the motor is caused to oscillate between two adjacent positions by a signal received along line 44 from a drive circuit 46.

The drive circuit 46 drives the stepping motor 23 in response to a signal received along line 48 from a microcomputer 50. As will be described in greater detail below, the microcomputer 50 controls the frequency with which the stepping motor 23 is driven, and thus also determines the frequency of oscillation of the valving element 14. The drive circuit 46 is a conventional interfacing circuit for the purpose of converting the relatively low amplitude signal received along line 48 from the microcomputer 50 to a signal which can be used to power and drive the stepping motor 23. The construction of a suitable drive circuit would be well-known to those skilled in the pertinent arts, and therefore the details of the drive circuit 46 need not be given here. It will also be appreciated that, since the motion of the valving element 14 is directly controlled by the microcomputer 50, the position of the former will always be "known" to the later. Thus, it will always be known to the computer whether the chopper valve 10 is in the "signal" state (radial bore 20 aligned with flow head pressure sensing port 16), or in the "reference" state (radial bore 20 aligned with reference pressure sensing port 18).

Referring once again to the differential pressure transducer 26, the electrical output signal from the transducer is, as previously mentioned, carried on output line 42 to a signal treatment circuit 52. In actuality, the signal treatment circuit may comprise a plurality of amplifying and filtering circuits, of types well-known in the art, which are used to amplify the relatively low-level output signal of the transducer 26, while removing noise and other extraneous signals therefrom.

From the signal treatment circuit 52, the electrical signal is fed along line 54 to a sample-and-hold circuit 56 which, again, may be of conventional design. The sample-and-hold circuit 56 is under the control of the microcomputer 50, receiving a control signal therefrom along line 58. When the sample-and-hold circuit 56 is in its sampling mode, it is receptive to the signal received from line 54. Upon receiving an appropriate command from the microcomputer 50, the sample-and-hold circuit 56 stores this signal for operation thereon by an analog-to-digital conversion circuit 60. The analog-to-digital converter 60 again may be of various conventional types, and serves to convert the analog signal to a digital form suitable for input to the microcomputer along the line 62. The microcomputer 50 can then process the digitized pressure-indicative signal, using stored programs and data, as well as data received from a data entry device 64 (e.g., a keyboard), to provide signals indicative of flow rate and instantaneous volume. (Further details of the microcomputer structure and function will be given below.) These flow rate and volume indicative signals are then conveyed along an output line 66 to an output put device such as a visual display device 68 (e.g., a CRT or printer).

Figure 2:
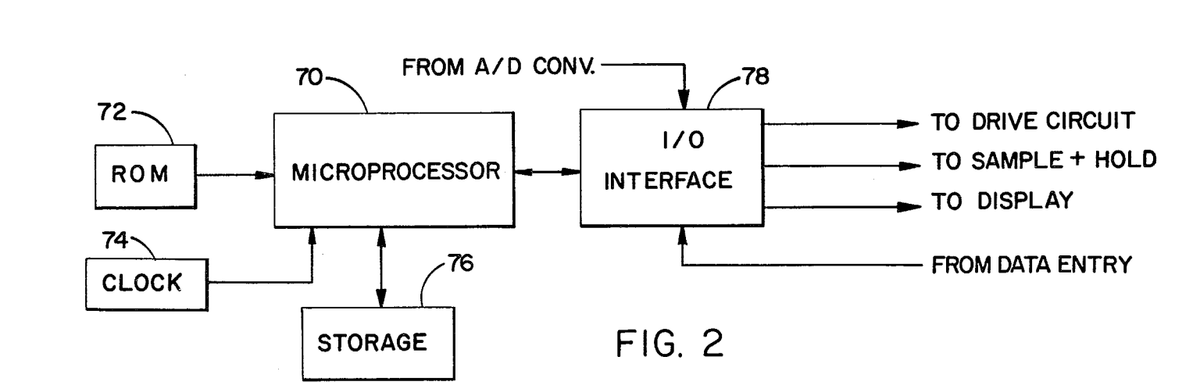
FIG. 2 is a schematic representation of the microcomputer used in the system of FIG. 1.
Figure 3:
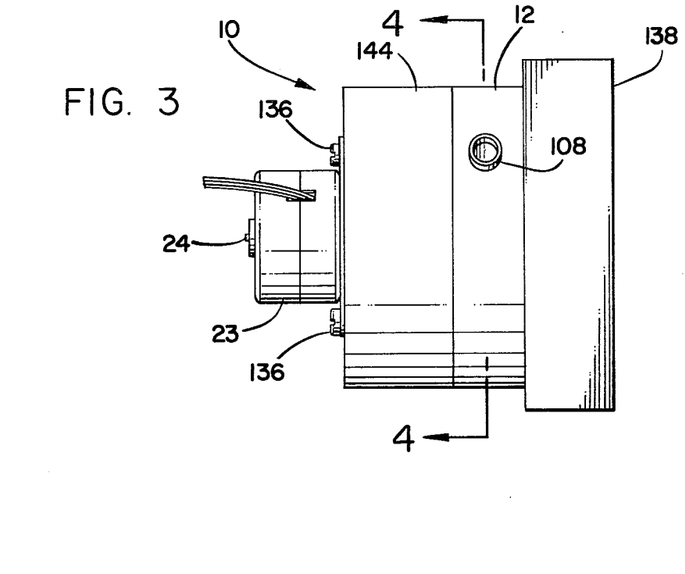
FIG. 3 is an elevational view of the oscillating chopper valve used in the system of FIG. 1.

FIG. 2 illustrates the microcomputer 50 broken down into its functional subsystems. Central to the microcomputer 50 is a microprocessor 70 which performs the required data processing functions. The microprocessor 70 receives inputs from a Read Only Memory 72, a real-time clock oscillator 74, a storage element (read/write memory) 76, and an input/output interface 78.

The Read Only Memory 72 contains the basic programs which control the operation of the microcomputer 50, as well as the programs for converting the digitized pressure-indicative signal, received from the analog-to-digital converter 60, into signals indicative of flow rate and volume. The real-time clock oscillator 74 provides a clock signal which controls the frequency of oscillation of the stepping motor 23. The clock 74 also determines the timing of the control signal, applied to the sample-and-hold circuit 56 along line 58, which controls the switching of the sample-and-hold circuit 56 between its sampling mode and its holding mode. Thus, the clock 74 in effect determines the sample rate of the system.

The read/write storage 76 advantageously contains both volatile and nonvolatile components. The volatile component may be used for the storage of data received from the data entry terminal 64, as well as for the temporary storage of the results of intermediate steps of the calculations performed by the microprocessor 70. The nonvolatile component of the storage element 76 is used for the semipermanent storage of a plurality of linearization constants, the values of which are calculated by means of a calibration routine, which, itself, can be stored in the Read Only Memory 72 for use when the microcomputer is selectively placed into a calibration mode.

The input/output interface 78 is a standard component in many microcomputer systems, and serves as a buffer and channel for directing output signals to the drive circuit 46, the sample-and-hold circuit 56, and the visual display device or devices 68. In addition, the input signals from the analog-to-digital converter 60 and the data entry terminal 64 are received by the input/output interface 78 for channeling to the microprocessor 70 and/or the storage element 76 as may be appropriate.

The structure of the gas flow measuring system having been described, its manner of operation will now be easily understood with reference to FIGS. 1 and 2.

In accordance with the clock signal generated by the clock oscillator 74 (or in actuality, a preselected submultiple of the clock oscillator frequency) the microcomputer 50 drives the stepping motor 23 in a first direction through the drive circuit 46. Although the first direction is arbitrary, let us assume that as a result of being driven in the first direction, the stepping motor 23 causes the oscillating valving element 14 to rotate so as to bring the radial bore 20 into communication with the flow head pressure inlet 16. (This position of the valve 10 will be referred to as the "signal mode.") The microcomputer 50, having driven the valve 10 to the signal mode, "knows" that the valve is in said mode and will remain so for a predetermined period of time, determined by the clock oscillator frequency.

With the valve 10 in the signal mode, pressure derived from the flow head 36 is transmitted to the signal side of the pressure transducer 26 through the axial bore 22 and the conduit 28, while at the same time the reference pressure is transmitted to the reference side of the transducer through the conduit 40. The resulting pressure differential across the transducer 26 produces a pressure-indicative output signal along line 42 which is received by the signal treatment circuit 52 for suitable amplification and filtering. The amplified and filtered pressure-indicative signal is then received from line 54 by the sample-and-hold circuit 56 when the latter is in its sampling mode of operation. The sample-and-hold circuit 56 then receives a control signal from the microcomputer 50 along the line 58. This control signal causes the sample-and-hold circuit to switch to its holding mode, in a manner well-known in the art, so that the previously sampled signal value can be transmitted to the analog-to-digital converter 60, for conversion to a digital signal. The digitized pressure-indicative signal is then transmitted along line 62 for input to the microcomputer 50, where it is processed in a manner to be described shortly.

The clock oscillator frequency is such that at a suitable time after the sample-and-hold circuit 56 is switched to its holding mode, the microcomputer 50, acting through the drive circuit 46, drives the stepping motor 23 in the opposite direction, thereby causing the valving element 14 to rotate so as to bring its radial bore 20 into communication with a reference pressure inlet 18. (This position of the valve 10 will be referred to as the "reference mode.") With the valve 10 in its reference mode, pressure on both sides of the differential pressure transducer 26 is equalized. The result is a signal having a reference value being produced along output line 42. As previously discussed, the level of this reference signal can change with time due to the effects of hysteresis and changes in ambient temperature. This reference signal is then processed by the signal treatment circuit 52 and sent to the sample-and-hold circuit 56, which has been previously switched back to its sampling mode by means of the control signal received from the microcomputer along the line 58. Upon receiving the reference signal, the sample-and-hold circuit 56 is once again switched back to its holding mode, as previously described, for digitizing of the signal by means of the analog-to-digital converter 60 and transmission to the microcomputer for processing. It will be remembered that, since the oscillating valving element 14 is under the control of the microcomputer, the latter always "knows" when the valve 10 has switched from its signal mode to its reference mode and vice versa, so that the sample-and-hold circuit 56 can be switched between its sampling mode and holding mode at the appropriate times via the control signal applied along line 58, thereby eliminating the need for a separate mechanism for determining the state of the valve 10.

It will be seen that the sample-and-hold circuit 56 will be switched through at least two complete sample-and-hold cycles for each mode-switching cycle of the valve 10, thereby allowing a sampling of both a pressure-indicative signal value when the valve is in the signal mode, and a reference signal value when the valve is in the reference mode. Thus, under the control of the microcomputer 50, the valve 10 is switched at a first switching frequency which is proportional to the frequency of the clock oscillator 74, while the sample-and-hold circuit 56 is switched at a second switching frequency at least double the first switching frequency and lagging behind the valve switching by a short delay to allow for the response times of the valve 10 and the transducer 26. In this manner, the microcomputer synchronizes the sampling intervals of the sample-and-hold circuit 56 with the incidence of reference-signal values and the pressure-indicative signal values. Since the microcomputer 50 controls both the mode-switching frequency of the valve 10 and the mode-switching frequency of the sample-and-hold circuit 56, and coordinates the latter to the former, the sampling rate of the system is limited only by the speed with which the valving element 14 can be oscillated, and by the aforementioned response times.

As previously mentioned, the microcomputer 50 processes the signal received from line 62 to derive output signals indicative of flow rate and accumulated volume, which signals are converted to some visible format by the display device or devices 68. The signal processing that is performed may be summarized as follows:

The values of the digitized pressure-indicative signals received from the input line 62 are stored by the microcomputer 50 in storage 76. These values represent alternating reference values and flow head pressure-indicative values. In practice, two consecutive reference values and an intervening flow head pressure value are temporarily stored. By using subtraction and numerical filtering operations well-known in the art, the average of the two reference values is subtracted from the intervening flow head pressure value to obtain a differential pressure value. This signal has thus been corrected to compensate for drifts in the reference level signal produced when the chopper valve 10 is in its reference mode.

The corrected differential pressure value is converted to an instantaneous flow rate value by means of a transfer function program stored in the Read-Only Memory 72. The particular transfer function used depends on the geometry of the flow head, and it is empirically derived by techniques well-known to those skilled in the pertinent arts. The transfer function may make use of linearization constants which compensate for nonlaminar flow patterns in the flow head and for minor variations in geometry between different flow heads of the same type. These linearization constants are derived by means of a calibration program which may be run by the microcomputer at an appropriate time before measurements are taken. Once derived, the linearization constants are then stored in the nonvolatile portion of the storage memory 76 for calling up by the transfer function program. Since the transfer function requires values for ambient data such as ambient pressure, temperature, and humidity, values for such data are called up from the volatile portion of the storage memory 76 after having been entered by a data entry device 64, such as a keyboard.

Finally, a value for the accumulated volume of flow is obtained by the microprocessor 70 using standard numerical integration techniques. Use is made of the sampling of the flow head measurements at known, equally spaced time intervals.

The microcomputer may be programmed to perform further manipulations of the basic flow and volume information. Such manipulations may be performed by an operating program stored in the Read Only Memory 72, or by routines entered by the user through the data entry device 64. As previously mentioned, the display device 68 can be used to display the derived values of flow rate, accumulated volume, and such other information as may be desired The system of FIGS. 1 and 2 having been described, attention can now be turned to the specific structure of the chopper valve 10, as illustrated in FIGS. 3 through 6.

As shown in FIGS. 3-6, the housing or body 12 of the oscillating chopper valve 10 is seen to include a coaxial annual extension 102, sharing an axial bore 104 with the valve body 12. The housing 12 contains a pair of radially directed bores 106. (See FIGS. 4 and 6.) Either of the bores 106 can function as the flow head pressure inlet 16, as shown in FIG. 1, with the other bore 106 serving as the reference pressure inlet 18. Each of the bores 106 communicates with a tubular fitting 108 for connection to the reference pressure conduit 38 and the flow head pressure conduit 32. For reasons which will presently be made clear, the bores 106 subtend and define an angle which is preferably in the range of approximately 150° to 160°, although this angle is not critical, due to the angles subtended by the internal diameters of the bores 106 and the radial valve bore 20. The housing 12, including the annular extension 102, is preferably made of an integral piece of lightweight, easily-machined plastic, such as the acetal resin plastic marketed by E. I. DuPont de Nemours & Co., Inc. under the name "Delrin."

The oscillating valving element 14 is a basically tubular body having a generally cylindrical, enlarged diameter portion 110, the outside diameter of which is slightly less than the inside diameter of the axial bore 104 in the valve body 12. The valving element 14 is provided with the previously described radial bore 20 and axial bore 22, with the radial bore 20 diametrically traversing the enlarged diameter portion 110. If the proximal end of the valving element 14 is defined as the end which is inserted into the axial bore 104, then the other end, which is thereby defined as the distal end, is provided with a radially extending rod or pin 112, the purpose of which will be explained later on. The valving element 14 is retained in the valve body 12 by means of a pair of annular bearing races 114, encompassing the proximal and distal ends of the valving element 14. The bearing races 114 may contain either roller bearings or ball bearings (not shown) to reduce friction, and to facilitate high speed operation even with a low-torque motor. To this end, it is also advantageous to construct the valving element 14 of a lightweight, easily-machined plastic, such as "Delrin," so as to provide a low moment of inertia.

Figures 5, 6:
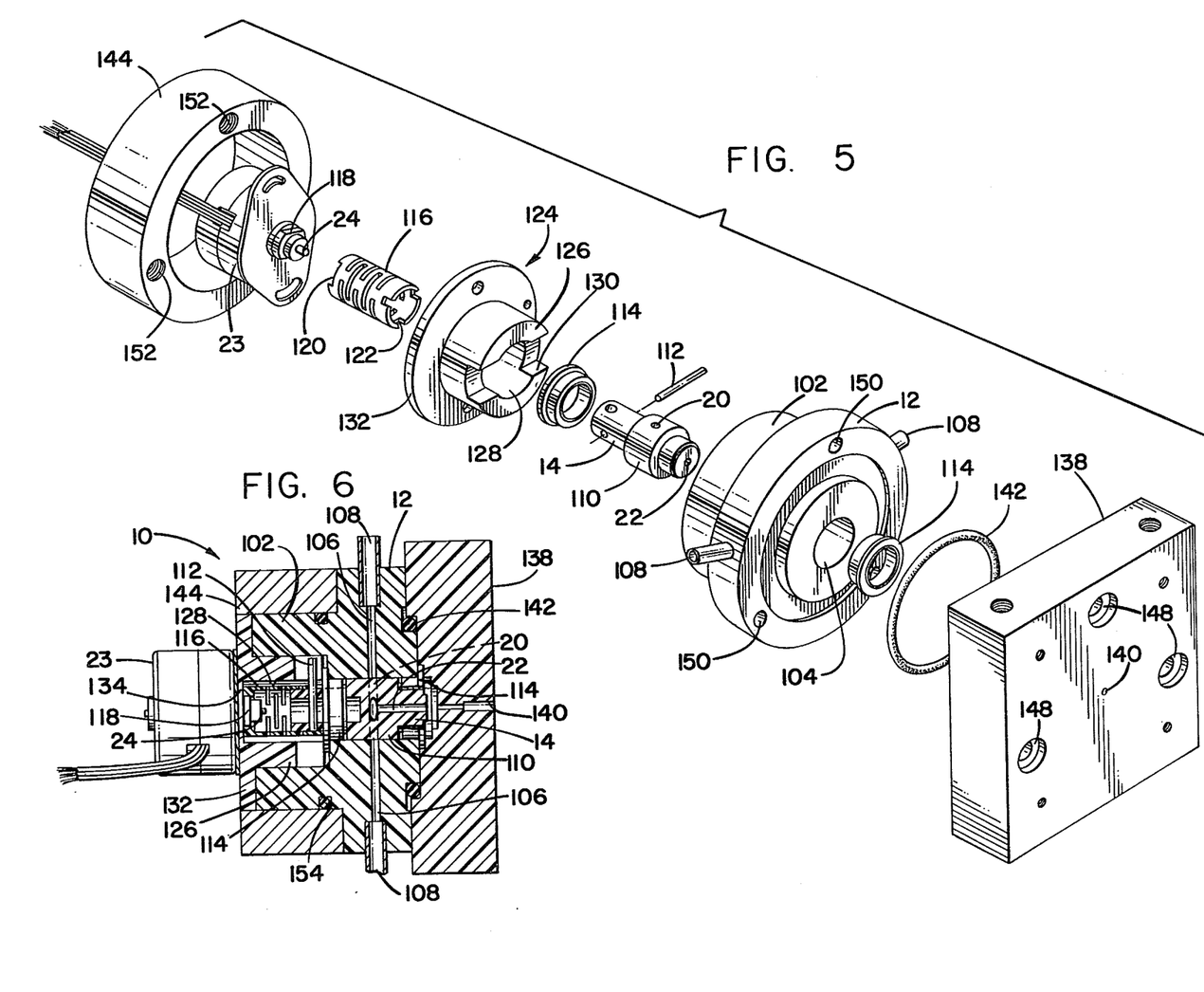
FIG. 5 is an exploded perspective view of the valve shown in FIG. 3.
FIG. 6 is a cross-sectional view along line 6—6 of FIG. 4.

The stepping motor 23, as previously described, has a shaft 24 which is connected to the distal end of the valving element 14 by means of a tubular coupler 116. The attachment of the shaft 24 to the coupler 116 is accomplished by means of a flat-sided key 118 on the shaft 24 which is engagable in a mating slot 120 on the distal end of the coupler 116. The proximal end of the coupler 116 is adapted to engage the exterior surface of the distal end of the valving element 14, and has one or more slots 122 adapted to accommodate the pin 112.

Figure 4:
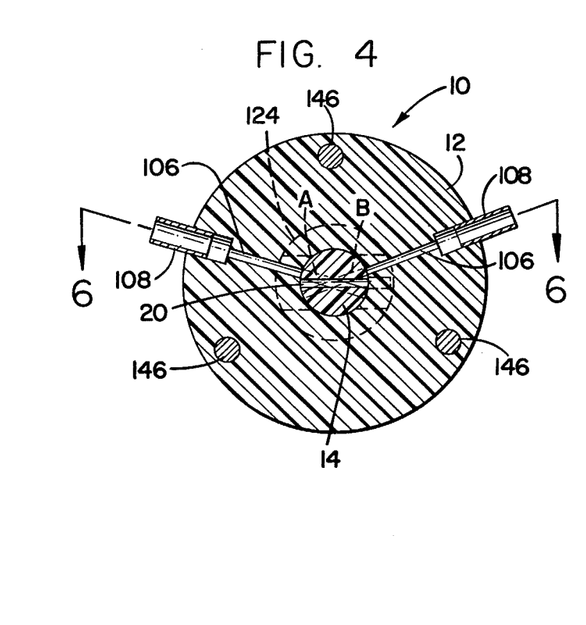
FIG. 4 is a cross-sectional view along line 4—4 of FIG. 3.

The oscillation of the valving element 14 by means of stepping motor 23 may be described with reference to FIG. 4. As previously discussed, the stepping motor is detented in a plurality of equally spaced positions along the shaft's path of rotation In a specific example of the invention which has been constructed, a stepping motor was used which was detented in twenty positions spaced apart by 18° of arc. The stepping motor is operated so as to oscillate between two adjacent detented positions. With the motor shaft 24 coupled to the valving element 14 in the manner previously described, the valving element will therefore be oscillated through 18° of arc. Thus, as can be seen in FIG. 4, when the stepping motor has been moved to what may be called its first detented position, the radial bore 20 of the valving element 14 will be in the position indicated by the dotted outline "A". In this position, the left end of the radial bore 20, as shown in FIG. 4, is aligned with the left side pressure inlet 106, while the right end of the bore 20 is out of alignment with the right side pressure inlet 106, so that the left pressure inlet 106 is open, and the right pressure inlet 106 is closed. When the motor is oscillated to what may be called its second detented position, the valving element 14 is in the position indicated by the dotted line "B", thereby opening the right pressure inlet through the right end of the radial bore 20, while the left end of the radial bore 20 is brought out of alignment with the left pressure inlet 106, thereby closing said pressure inlet. It will be appreciated from this description that, if the detented positions of the motor are 18° apart, the two inlet bores 106 should be spaced apart by 162°. However, in actual practice, there will be a tendency toward a slight overshoot of the detented positions, so that, for the example given, the pressure inlet bores 106 are spaced apart by approximately 152°. Moreover, even this angle is not critical, since it is only necessary partially to open the pressure inlet bores 106. Of course, these figures are given by way of example only, and other angular dimensions may be used to accommodate different stepping motors and different specific valve configurations.

Since the stepping motor has several pairs of detented positions, it is necessary to assure proper alignment of the valving element 14, pressure inlet bores 106, and motor detent positions during times when motor power is off. For this purpose, a locator element 124 is used. As best shown in FIG. 5, the locator element 124 comprises a tubular body 126 having a central axial bore 128 dimensioned slightly larger than the outside diameter of the coupling element 116, as seen in FIG. 6, so as to maintain a clearance therebetween. The end face of the tubular body 126 is provided with a transverse slot or channel 130, which is dimensioned so that its interior walls act as end stops for the pin 112 at the extremes of travel of the valving element 14. The distal end of the locator 124 is provided with a circular disc 132 which acts as an alignment plate for the distal end of the annular extension 102 of the valve body 12, while also providing a mounting plate for the stepping motor 23. Thus, the disc 132 is provided with a central aperture 134 dimensioned to accommodate the shaft 24 and shaft key 118 of the stepping motor 23. Advantageously, screws 136 (FIG. 3) or other fastening means used to secure the stepping motor 23 to the disc 132 can also be used to attach the locator element 124 to the distal face of the valve body extension 102.

The proximal face of the valve body 12 is covered by, and attached to, an end block 138 having a reduced diameter transverse passage 140 therethrough communicating with the axial bore 22 of the valving element 14. In use, the bore 140 is connected in fluid communication with the conduit 28 (FIG. 1) leading to the signal side of the differential pressure transducer 26. The juncture between the end block 138 and the valve body 12 may advantageously be sealed with an O-ring 142 seated in appropriately dimensioned grooves in the adjacent end block and valve body surfaces. An annular retainer ring 144 advantageously encircles the valve body extension 102 and the periphery of the disc 132, abutting against the distal shoulder formed between the valve body 12 and its extension 102, as shown in FIG. 6. The retainer ring 144, valve body 12, and end block 138 are all secured to one another by means of screws 146 (FIG. 4) passing through holes 148, 150, and 152 in the end block 138, valve body 12, and retainer ring 144, respectively. Of course, other attachment means may be used as will be apparent to those skilled in the pertinent arts. Redundant sealing between the retainer ring 144 and the valve body extension 102 may be provided with an optional O-ring 154 seated in an annular groove around the periphery of the valve body extension 102.

There are several distinct advantages to the valve construction described above, as compared with prior art rotary (360°) chopper valves. First, by using an oscillating movement through only a few degrees (i.e., in the range of about 15° to 30°), rather than a rotational movement of a full 360°, faster valve action is possible, thereby enabling faster sampling rates and thus higher accuracy. Furthermore, by using an oscillatory action rather than a unidirectional rotational action, a phenomenon known as "pumping," associated with rotary chopper valves, is minimized. This "pumping" phenomenon, believed to be a result of the unidirectional rotational movement of the valving element, added a distortional component to the pressure signal transmitted from the chopper valve to the pressure transducer in prior art systems. Still another advantage of the novel valve construction of the present invention is the use of only two well-defined, detented valve positions, which facilitates valve state determination by the microcomputer which, itself, drives the valve element, rather than by a separate, external valve state determining mechanism.

What is claimed is:
1. A gas flow measuring system, comprising:
   flow head means for developing a flow-related pressure in response to a flow of gas;
   valving means, having an outlet port and first and second inlet ports, said first inlet port adapted for receiving a selected reference pressure, said second inlet port connected to said flow head means to receive said flow-related pressure therefrom, said valving means being movable between a first position in which said first inlet port communicates with said outlet port, and a second position in which said second inlet port communicates with said outlet port;
   a differential pressure transducer having a first pressure port adapted for receiving said selected reference pressure and a second pressure port in fluid communication with said outlet port, said transducer being adapted to produce an analog electrical signal having a reference value when said valving means is in said first position and a pressure-indicative value when said valving means is in said second position;
   means for generating a clock signal having a selected frequency;
   driving means, responsive to said clock signal, for moving said valving means between said first and second positions with a first switching frequency proportional to said selected frequency;
   sampling means, responsive to said clock signal, for receiving said analog electrical signal only during sampling intervals established periodically with a second switching frequency at least double said first switching frequency and coordinated therewith so that said sampling intervals occur when said analog electrical signal has either said reference value or said pressure-indicative value;
   digitizing means, electrically coupled to said sampling means, for converting the sampled analog electrical signal to a digital electrical signal during holding intervals established between successive ones of said sampling intervals; and
   signal processing means for processing said digital electrical signal to yield a signal indicative of the flow rate of gas through said flow head means.

2. The system of claim 1, wherein said valving means comprises a chopper valve adapted for oscillation between said first and second positions, and wherein said driving means comprises a stepping motor having a shaft operatively connected to said chopper valve to oscillate said valve between said first and second positions, each of said first and second positions corresponding to a detented position in the path of rotational movement of said shaft.

3. The system of claim 1, wherein said sampling means comprises a sample-and-hold circuit, having a sampling mode and a holding mode, and said signal processing means further comprises:
   control means responsive to said clock signal, for alternately enabling said sampling and holding modes with said second switching frequency, whereby said sampling mode is enabled when said analog electrical signal has said reference value or said pressure-indicative value, and said holding mode is enabled during intervals occurring between successive sampling mode enablements.

4. The system of claim 3, wherein said driving means comprises:

a motor operatively connected to said valving means; and motor actuation means, responsive to said clock signal, for driving said motor alternately in first and second directions with said first switching frequency, whereby said valving means is moved alternately to said first and second positions with said first switching frequency.

5. The system of claim 4, wherein said signal processing means further comprises:

first means responsive to said clock signal, for establishing said first and second switching frequencies and coordinating said control means with said motor actuation means so that said sampling mode is enabled substantially in synchronism with the incidence of either a pressure-indicative value or a reference value for said analog electrical signal;

second means for storing an operative program;

third means for receiving and storing inputted data; and fourth means, responsive to said digitized signal, said operative program, and said inputted data, for processing said digitized signal to yield said flow rate indicative signal.

6. The system of claim 5, wherein said signal processing means further comprises:

fifth means for processing said flow rate indicative signal to yield a volume-indicative signal.

7. The system of claim 3, wherein said sample-and-hold circuit holds the previously sampled value of said analog electrical signal during said holding mode, and wherein said digitizing means is operative on said previously sampled signal value during said holding mode.

8. In a gas flow measuring system, of the type employing a flow head for developing a flow-related pressure in response to a flow of gas, a pressure transducer for converting said flow-related pressure to an electrical signal, and signal processing means for converting said electrical signal to a flow rate-indicative signal, the improvement comprising:

valving means connected between said pressure transducer and said flow head, and movable between first and second positions, for (a) communicating said flow-related pressure to said transducer in said first position and (b) communicating a selected reference pressure to said transducer in said second position, whereby said electrical signal produced by said transducer has a pressure-indicative value when said flow-related pressure is communicated to said transducer, and a reference value when said reference pressure is communicated to said transducer by said valving means;

driving means for moving said valving means alternately between said first and second positions in response to a first control signal;

signal sampling means for receiving said electrical signal during sampling intervals established in response to a second control signal;

control means for generating said first and second control signals and coordinating said second control signal with said first control signal such that said sampling intervals occur substantially in synchronism with the incidence of said pressure-indicative values and said reference values of said electrical signal; and electronic means for transmitting the signal values received by said signal sampling means during said sampling intervals to said signal processing means.

9. The system of claim 8, wherein said valving means comprises:

a housing having a first port adapted for receiving said flow-related pressure and a second port adapted for receiving said reference pressure;

a movable valving element in said housing and having first and second intersecting bores, and adapted for movement between said first and second positions whereby said first bore is in fluid communication with said first port when said valving element is in said first position and with said second port when said valving element is in said second position; and means for communicating pressure from said second bore to said transducer.

10. The system of claim 9, wherein said driving means comprises:

a stepping motor having a shaft operatively connected to said valving element, said shaft being rotatable between at least two preselected rotational positions; and motor actuation means, responsive to said first control signal, for driving said motor so as to oscillate said shaft alternately between said first and second rotational positions, thereby causing said valving element to oscillate between said first and second positions with a valve-switching frequency determined by said first control signal.

11. The system of claim 10, wherein said second control signal establishes said sampling intervals with a sampling frequency at least double said valve-switching frequency.

12. The system of claim 8, wherein said signal sampling means has a sampling mode and a holding mode, said sampling intervals being established during enablement of said sampling mode, said sampling mode and said holding mode being alternately enabled in response to said second control signal.

13. The system of claim 12, wherein said signal sampling means holds at least one previously sampled value of said electrical signal during said holding mode, and said electronic means is responsive to said signal sampling means substantially only during said holding mode to transmit said previously sampled signal value to said signal processing means.

14. The system of claim 8, wherein said electrical signal is an analog signal, and said electronic means further comprises:

digitizing means, responsive to said signal sampling means during holding intervals established between successive ones of said sampling intervals for converting said analog signal to a digital signal; and means for transmitting said digital signal to said signal processing means.

15. The system of claim 8, further comprising:

damping means, connected between said valving means and said flow head, for damping acoustic waves propagated by the movement of said valving means.

16. The system of claim 8, further comprising:

filtering means, connected between said valving means and said transducer, for substantially blocking high frequency pressure transients from said transducer.

17. In a gas flow measuring system, of the type employing a flow head for developing a flow-related pressure in response to a flow of gas, a pressure transducer for converting said flow-related pressure to an electrical signal, and signal processing means for converting said electrical signal to a flow rate indicative signal, the improvement comprising:

valving means, connected between said pressure transducer and said flow head, and movable between first and second positions, for (a) communicating said flow-related pressure to said transducer in said first position, and (b) communicating a selected reference pressure to said transducer in said second position, whereby said electrical signal produced by said transducer has a pressure-indicative value when said flow-related pressure is communicated to said transducer, and a reference value when said reference pressure is communicated to said transducer by said valving means;

valve-driving means, operatively connected to said valving means, for oscillating said valving means between said first and second positions with a selected frequency; and     electronic means for (a) receiving said electrical signal during sampling intervals occurring substantially in synchronism with the incidence of said pressure-indicative values and said reference values, and (b) transmitting said pressure-indicative values and said reference values to said signal processing means.

18. The system of claim 17, wherein said valve-driving means comprises:

a reversible stepping motor having a shaft operatively connected to said valving means, said shaft being rotatable between at least two preselected rotational positions; and     motor-actuation means for alternately driving said motor in first and second directions with said selected frequency so as to oscillate said shaft between two adjacent ones of said at least two preselected rotational positions with said selected frequency.

19. The system of claim 17, wherein said valving means comprises:

a housing having a first inlet adapted for receiving said flow-related pressure and a second inlet adapted for receiving said selected reference pressure;

a valving element, rotatably mounted in said housing, and having first and second intersecting bores, and adapted for rotational oscillation between said first and second positions, whereby said first bore receives (a) said flow-related pressure from said first inlet when said valving element is in said first position, and (b) said selected reference pressure from said second inlet when said valving element is in said second position, the intersection between said first and second bores allowing the communication to said second bore of the pressure communicated to said first bore; and     means for communicating pressure from said second bore to said transducer.

* * * * *